US012644894B1

(12) United States Patent
Alterki et al.

(10) Patent No.: US 12,644,894 B1
(45) Date of Patent: Jun. 2, 2026

(54) IDENTIFICATION OF PROTEIN BIOMARKERS FOR DIAGNOSIS AND TREATMENT FOR SLEEP APNEA

(71) Applicants: Sabah Al-Ahmad Center for Giftedness and Creativity, Safat (KW); Dasman Diabetes Institute, Dasman (KW)

(72) Inventors: Abdulmohsen Alterki, Dasman (KW); Fahd Al-Mulla, Dasman (KW); Jehad Ahmed Abubaker, Dasman (KW); Mohamed Abu-Farha, Dasman (KW)

(73) Assignees: Sabah Al-Ahmad Center for Giftedness and Creativity, Safat (KW); Dasman Diabetes Institute, Dasman (KW)

( * ) Notice: Subject to any disclaimer, the term of this patent is extended or adjusted under 35 U.S.C. 154(b) by 0 days.

(21) Appl. No.: 19/279,380

(22) Filed: Jul. 24, 2025

Related U.S. Application Data

(63) Continuation of application No. 19/209,984, filed on May 16, 2025, now abandoned.

(51) Int. Cl.
*G01N 33/68* (2006.01)
*A61B 5/00* (2006.01)

(52) U.S. Cl.
CPC ....... *G01N 33/6893* (2013.01); *A61B 5/4818* (2013.01); *G01N 33/6848* (2013.01); *G01N 2570/00* (2013.01); *G01N 2800/2864* (2013.01)

(58) Field of Classification Search
None
See application file for complete search history.

(56) References Cited

U.S. PATENT DOCUMENTS

2009/0307181 A1   12/2009   Colby et al.
2019/0147982 A1   5/2019   Gozal et al.

FOREIGN PATENT DOCUMENTS

AU      2006308812    *   5/2007   ............. G01N 33/68
WO    WO 2017194499   *  11/2017   .............. C12Q 1/68

OTHER PUBLICATIONS

Ambati, A. et al., "Proteomic biomarkers of sleep apnea", SleepJ 1-12 Publication date: May 5, 2020.
Bikov, A., et al., "Coagulation and Fibrinolysis in Obstructive Sleep Apnoea", Int. J. Mol. Sci. 22 (2834) Publication date: Mar. 11, 2021.
Cederberg, K. L. J., et al., "Proteomic Biomarkers of the Apnea Hypopnea Index and Obstructive Sleep Apnea: Insights into the Pathophysiology of Presence, Severity, and Treatment Response", Int. J. Mol. Sci. 23:7983 Publication date: Jul. 20, 2022.
Jurado-Gamez, B., et al. "Serum proteomic changes in adults with obstructive sleep apnoea", Jounral of Sleep Research 21(2): pp. 139-146 Publication date: Sep. 17, 2011 (Abstract provided).
Xu, H. et al., "Chromatography/Mass Spectrometry-Based Biomarkers in the Field of Obstructive Sleep Apnea" Medicine 94(40) Publication date: Oct. 2015.

* cited by examiner

*Primary Examiner* — Ann Montgomery
(74) *Attorney, Agent, or Firm* — Nath, Goldberg & Meyer; Joshua B. Goldberg

(57) ABSTRACT

The present subject matter relates to a method of diagnosing and treating sleep apnea (SA) in a patient. The method may include determining whether the patient needs a polysomnography (PSG) by obtaining a biological sample from the patient to determine if the subject has a protein selected from the group consisting of B3GNT2, LDHA, and H6PD/G6PE. The expression of one of the proteins may be associated with the presence of SA in a patient. If the patient has a protein associated with the presence of SA, then the method includes conducting a Polysomnography (PSG) on the patient to further determine if the patient has SA. If the patient is further determined to have SA, the method may then include treating the patient with a treatment of SA selected from the group consisting of ENT multilevel surgery, continuous positive airway pressure (CPAP) therapy, and bariatric surgery.

12 Claims, 4 Drawing Sheets

Specification includes a Sequence Listing.

IDENTIFICATION OF PROTEIN BIOMARKERS FOR DIAGNOSIS AND TREATMENT FOR SLEEP APNEA

CROSS-REFERENCE TO RELATED APPLICATION

This application is a continuation of U.S. patent application Ser. No. 19/209,984, filed on May 16, 2025, the entire contents of which are incorporated herein by reference.

SEQUENCE LISTING

The instant application contains a Sequence Listing which has been submitted in XML format via Patent Center and is hereby incorporated by reference in its entirety. Said XML copy, created on Apr. 9, 2025, is named 3306088SEQ.xml and is 4,632 bytes in size.

BACKGROUND

1. Field

The present disclosure relates to a method for diagnosing and treatment of sleep apnea.

2. Description of the Related Art

Sleep Apnea (SA) is a prevalent condition characterized by repetitive episodes of complete or partial upper airway obstruction during sleep, leading to reduced oxygen saturation and disrupted sleep. Currently, the diagnosis of Sleep Apnea (SA) is primarily reliant on Polysomnography (PSG), which is costly and not widely accessible. Furthermore, there is a lack of reliable biomarkers to assist with diagnosis of SA or predict treatment response in SA patients. There is an urgent need for non-invasive, accessible biomarkers that can aid in the diagnosis of SA and predict the efficacy of various treatments, including ENT (ear, nose, and throat) multilevel surgery, continuous positive airway pressure (CPAP) therapy, and bariatric surgery.

Thus, new methods of diagnosing SA and solving the aforementioned problems are desired.

SUMMARY

The present subject matter relates to medical diagnostics and treatment, with a focus on identifying proteins predictive of Sleep Apnea (SA). These proteins can be used to determine the need for a sleep study and assess the effectiveness of subsequent treatments. SA affects approximately 20% of the population and is strongly linked to conditions such as diabetes, cardiovascular disease, heart dysfunction, obesity, metabolic disorders, and increased mortality risk. Most people with SA remain undiagnosed and untreated due to the limited availability of sleep labs, high costs, and inaccessibility. A simple, well-validated test capable of detecting proteins useful in the diagnosis and treatment of SA may enable mass screening, allowing early and accurate identification of individuals who need sleep studies and appropriate treatment.

The present subject matter relates to a method of diagnosing and treating sleep apnea (SA) in a patient. The method may include determining whether the patient needs a polysomnography (PSG) by obtaining a biological sample from the patient and performing or having performed next-generation sequencing (NGS) to determine if the subject has a diagnostic level of an amino acid sequence comprising a sequence at least 95% identical to a protein selected from the group consisting of B3GNT2, LDHA, and H6PD/G6PE. The expression of one of the proteins may be associated with the presence of SA in a patient. If the patient has a protein associated with the presence of SA, the method may include conducting a Polysomnography (PSG) on the patient to further determine if the patient has SA. If the patient is further determined to have SA, the method may include treating the patient with a treatment of SA selected from the group consisting of ENT multilevel surgery, continuous positive airway pressure (CPAP) therapy, and bariatric surgery.

The method may further include taking an additional biological sample from the patient in a timeframe of 3 months to 6 months after the treatment of SA and detecting a new level of the protein. If no difference in the new level of the protein is detected, then the method may include administering a new treatment for SA to the patient.

These and other features of the present subject matter will become readily apparent upon further review of the following specification.

DETAILED DESCRIPTION OF THE PREFERRED EMBODIMENTS

Figures 1, 2A:
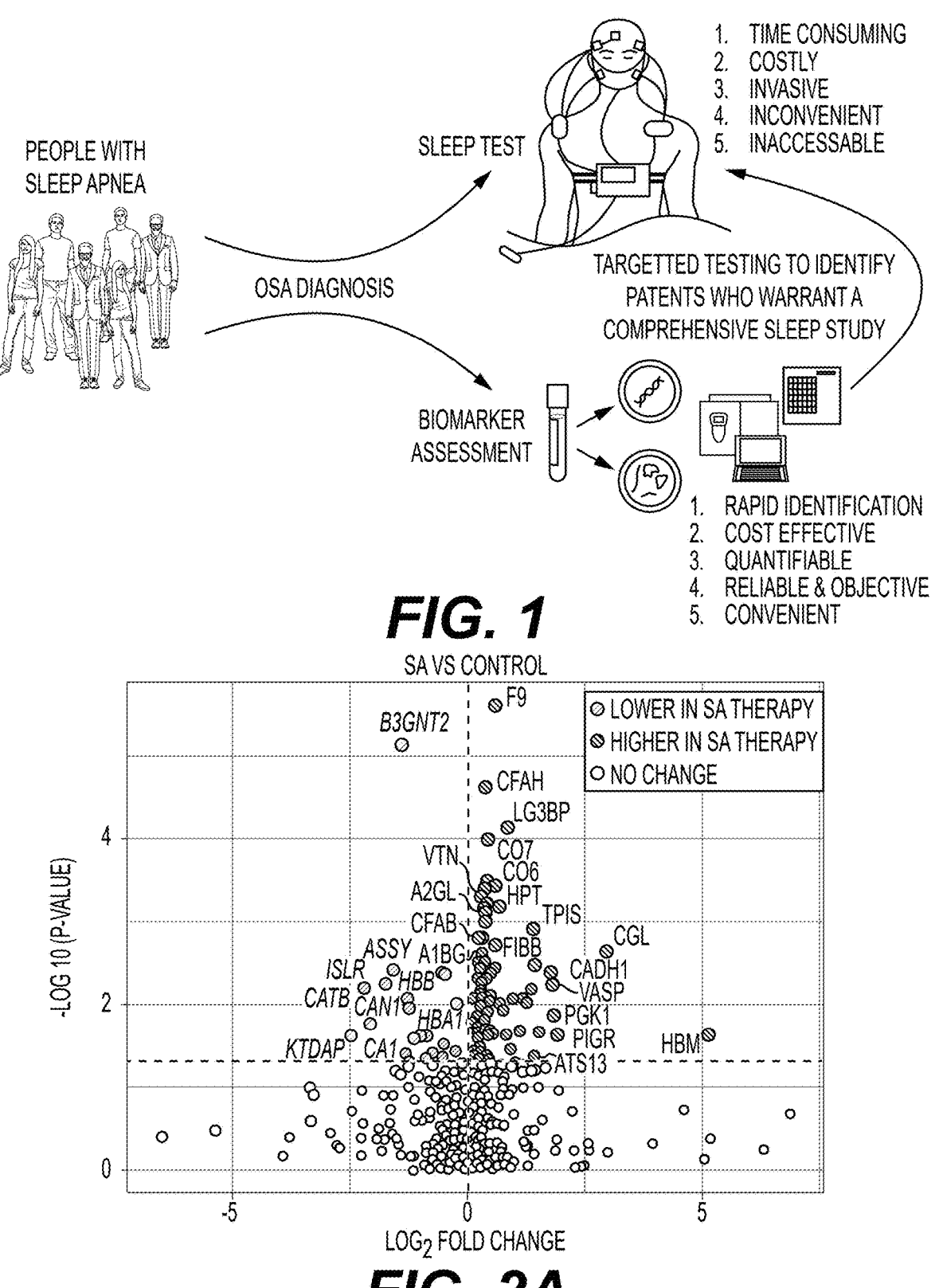
FIG. 1 is a diagram of biomarker screening with Sleep testing for sleep SA diagnosis.
FIG. 2A is a graph showing protein expression in a control group compared with individuals diagnosed with SA.

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a +10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as sleep apnea or obstructive sleep apnea.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to medical diagnostics and treatment, with a focus on identifying proteins predictive of SA. These proteins can be used to determine the need for a sleep study and assess the effectiveness of subsequent treatments. SA affects approximately 20% of the population and is strongly linked to conditions such as diabetes, cardiovascular disease, heart dysfunction, obesity, metabolic disorders, and increased mortality risk. Most people with SA remain undiagnosed and untreated due to the limited availability of sleep labs, high costs, and inaccessibility. A simple, well-validated test capable of detecting protein signatures for SA would enable mass screening, allowing proper identification of individuals who need sleep studies and appropriate treatment (FIG. 1).

Furthermore, these proteins could be tracked over time to monitor treatment efficacy and guide adjustments as needed. The method described herein may be used by all health care providers, including doctors dealing with patients diagnosed with sleep apnea, sleep disturbances, prediabetes, diabetes, cardiovascular disease, obesity, sexual and metabolic dysfunctions. In addition, biosensors and biomonitoring devices (point-of-care diagnostics) that detect any combination or all the Proteins from bodily fluids may be used directly by individuals for self-diagnosis.

The present subject matter relates to a method of diagnosing and treating sleep apnea (SA) in a patient. The method may include determining whether the patient needs a polysomnography (PSG) by obtaining a biological sample from the patient and performing or having performed next-generation sequencing (NGS) to determine if the subject has a diagnostic level of an amino acid sequence comprising a sequence at least 95% identical to a protein selected from the group consisting of B3GNT2, LDHA, and H6PD/G6PE. The expression of one of the proteins may be associated with the presence of SA in a patient. If the patient has a protein associated with the presence of SA, the method may include conducting a Polysomnography (PSG) on the patient to further determine if the patient has SA. If the patient is further determined to have SA, the method may include treating the patient with a treatment of SA selected from the group consisting of ENT multilevel surgery, continuous positive airway pressure (CPAP) therapy, and bariatric surgery.

The amino acid sequence of the protein B3GNT2 comprises:

1   msvgrrrikl   lgilmmvnvf   iylivevsks   ssqekngkge
     viipkekfwk isdppvaywn
61   reqeklnrry   npilntlanq   tgdvygfsni   shlnfcepdl
     rvmsvvsgfs nlpdrfkdfl 5                                                                6

121 lylrcrnysl lidqpdkcak kpflllaiks liphfarrqa ireswgretn
    vgnqtvvrvf
181 llgqtppedn hpdlsdmlkf esekhqdilm wnyrdtffnl slkev-
    lflrw vstscpnaef
241  vfkgddddvfv  nthhilnyln  slpknkakdl  figdvihnag
phrdkklkyy ipevvytgvy
301 ppyaggggfl ysghlalrly nitdqvllyp iddvytgmcl qklglv-
    pekh kgfktfdiee
361 knknnicsyv dlmlvhsrkp qemidiwsrl qnahlnc (SEQ ID
    NO: 1)
The amino acid sequence of the protein LDHA comprises:
1 matlkdqliy nllkeeqtpq nkitvvgvga vgmacaisil mkdlad-
    elal vdviedklkg
61   emmdlqhgsl   flrtpkivsg   kdynvtansk   lviitagarq
    qegesrlnlv qrnvnifkfi
121 ipnvvkyspn cklivsnpv diltyvawki sgfpknrvig sgcnld-
    sarf rylmgerlgv
181 hplschgwvl gehgdssvpv wsgmnvagvs lktlhpdlgt dkd-
    keqwkev hkqvvesaye
241  viklkgytsw  aiglsvadla  esimknlrrv  hpvstmikgl
ygikddvfls vpcilgqngi
301 sdlvkvtlts eeearlkksa dtlwgiqkel qf (SEQ ID NO: 2)
The amino acid sequence of the protein H6PD/G6PE
comprises:
1 maeqvalsrt qvcgilreel fqgdafhqsd thifiimgas gdlakkkiyp tiwwlfrdgl
61 lpentfivgy arsrltvadi rkqsepffka tpeeklkled ffarnsyvag
    qyddaasyqr
121lnshmnalhl gsqanrlfyl alpptvyeav tknihescms qigwn-
    riive kpfgrdlqss
181drlsnhissl   fredqiyrid   hylgkemvqn   lmvlrfanri
    fgpiwnrdni acviltfkep
241  fgtegrggyf  defgiirdvm  qnhllqmlcl  vamekpastn
    sddvrdekvk vlkcisevqa
301nnvvlgqyvg npdgegeatk gylddptvpr gsttatfaav vlyvenerwd gvpfilrcgk
361alnerkaevr   lqfhdvagdi   fhqqckrnel   virvqpneav
    ytkmmtkkpg mffnpeesel
421dltygnrykn vklpdayerl ildvfcgsqm hfvrsdelre awrift-
    pllh qielekpkpi
481 pyiygsrgpt eadelmkrvg fqyegtykwv nphkl (SEQ ID
    NO: 3)
In an embodiment, the diagnostic level of expression of
the protein in a patient may be based on a level of the protein
in a group of patients that tested positive for SA in a PSG.
In various embodiments, the biological sample may be
selected from the group consisting of plasma, blood, urine,
and saliva. In particular embodiments, the biological sample
may be plasma.
    In other embodiments, the method may further include
taking an additional biological sample from the subject in a
timeframe of 3 months to 6 months after the treatment of SA
and detecting a new level of the protein associated with SA.
If no difference in the new level of the protein is detected,
then the method may include administering a new treatment for SA to the patient.
    In another embodiment, the present subject matter may
relate to a method of diagnosing and treating SA in a patient.
The method may include obtaining a biological sample from
the subject and detecting in the biological sample the
presence of a protein selected from the group consisting of
B3GNT2, LDHA, and H6PD/G6PE. The presence of one of
the proteins may be associated with the presence of SA in the
patient based on a level of the protein in patients that tested
positive for SA in a PSG. If the presence of the protein is
detected in the patient at a level associated with SA, then the
method may include treating the patient with a treatment of SA selected from the group consisting of ENT multilevel
surgery, continuous positive airway pressure (CPAP)
therapy, and bariatric surgery.
    In various embodiments, the biological sample may be
selected from the group consisting of plasma, blood, urine,
and saliva. In particular embodiments, the biological sample
is plasma.
    In some embodiments, the method may further include
taking an additional biological sample from the subject in a
timeframe of 3 months to 6 months after the treatment of
OSA and detecting a new level of the protein. If no differ-
ence in the new level of the protein is detected, then a new
treatment may be administered to the patient.
    In other embodiments, the biological sample may be
tested using mass spectrometry (MS) for proteomics. In
various embodiments, testing for levels of various proteins
may be performed using any means now known or devel-
oped in the future to detect proteins.
    In still other embodiments, the treatment of SA used may
be based on the protein detected.

EXAMPLES

Figure 2B:
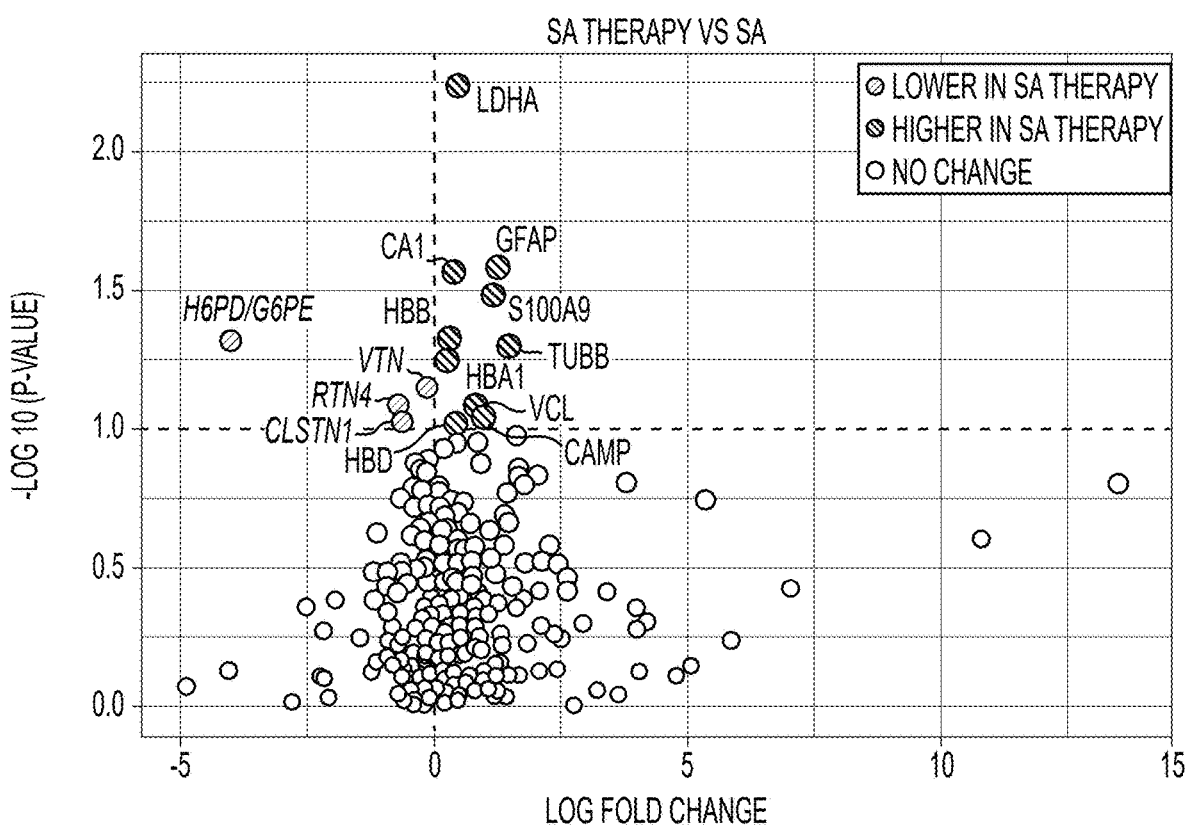
FIG. 2B is a graph showing protein expression in patients having undergone therapy for SA compared with individuals diagnosed with SA.
Figure 2C:
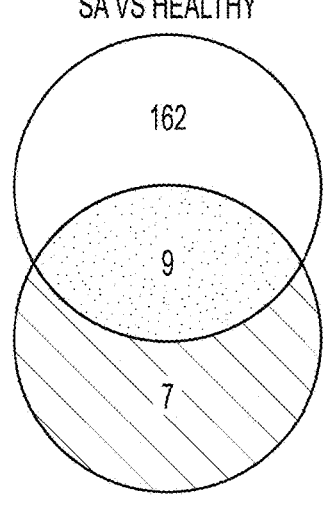
FIG. 2C is a Venn-diagram showing the overlap of proteins expressed in SA diagnosis vs Healthy Individuals and SA therapy with SA diagnosis.
Figure 2D:
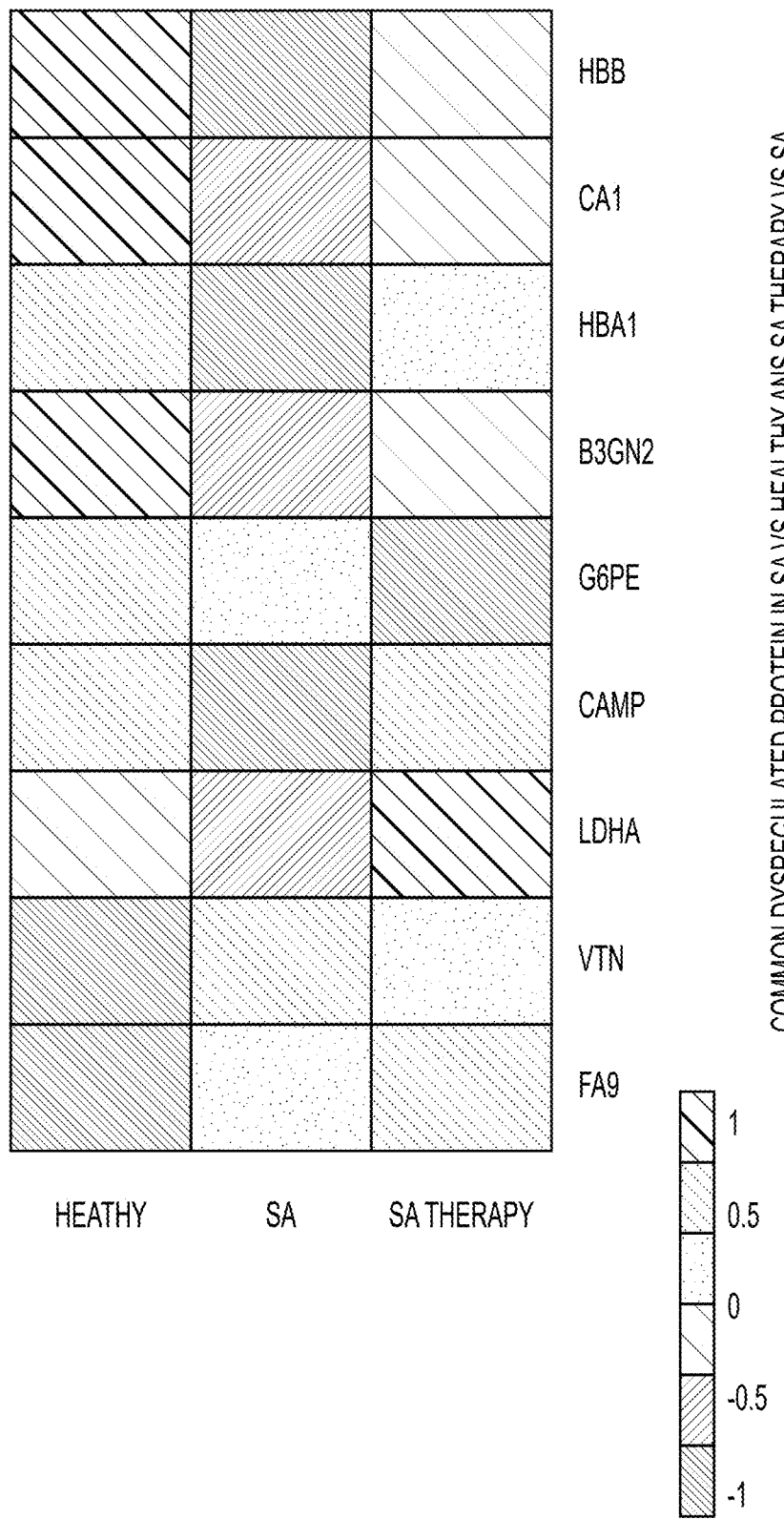
FIG. 2D shows the levels of expression of proteins in Healthy Individuals, Individuals Diagnosed with SA and individuals that have undergone SA therapy.

To detect the protein in samples from patients and healthy
controls, mass spectrometry (MS) for proteomics analyses,
specifically the Q-Exactive HF LC-ESI-MS/MS system
from Thermo Fisher Scientific.
    Proteins were extracted from plasma samples collected
from SA patients before and after intervention, as well as
from healthy controls. The extracted proteins were further
purified and quantified using mass spectrometry for pro-
teomic and metabolic profiling analyses. Proteins that were
differentially expressed and associated with SA were
selected for further analysis to validate their diagnostic
potential.
    The levels of proteins were measured in both SA patients
and healthy controls at the time of diagnosis (FIG. 2A), and
their diagnostic potential was compared to polysomnogra-
phy, the gold standard methods for sleep apnea diagnosis.
Additionally, these molecules were evaluated in SA patients
after 3-6 months of intervention to assess their response to
treatment (FIG. 2B).
    FIG. 2C is a Venn-diagram showing the overlap of nine
protein between patients diagnosed with SA and healthy
individuals compared with patients that have undergone
therapy for SA and patients diagnosed with SA. The data is
also shown in Table 1. Finally, the level of expression of the
protein in each of the three groups, healthy, SA, and SA
therapy, is shown in FIG. 2D.

TABLE 1

|  |  | SA vs Healthy | | SA therapy vs SA | |
| --- | --- | --- | --- | --- | --- |
| S. No. | Protein | log2(FC) | pvalue | log2(FC) | pvalue |
| 1 | LDHA | 0.40 | 0.012 | 0.47 | 0.003 |
| 2 | CA1 | −1.22 | 0.02 | 0.40 | 0.013 |
| 3 | VTB | 0.36 | 0.0002 | 0.01 | 0.047 |
| 4 | HBA1 | −1.20 | 0.005 | 0.27 | 0.020 |
| 5 | G6PE | 2.98 | 0.03 | −4.00 | 0.024 |
| 6 | HBB | −1.24 | 0.004 | 0.31 | 0.023 |
| 7 | B3GN2 | −1.39 | 0.000003 | 0.10 | 0.038 |
| 8 | CAMP | −1.24 | 0.049 | 0.99 | 0.046 |
| 9 | F9 | 0.61 | 0.00001 | 0.00 | 0.049 |

Common dysregulated protein in SA vs healthy and SA therapy vs SA

The treatment response was assessed after a minimum
follow-up period of 3 months post-intervention, with an average follow-up duration of 5 months. This timeframe is generally sufficient, based on earlier reports, to observe the necessary changes or improvements resulting from therapy.

Figure 3A:
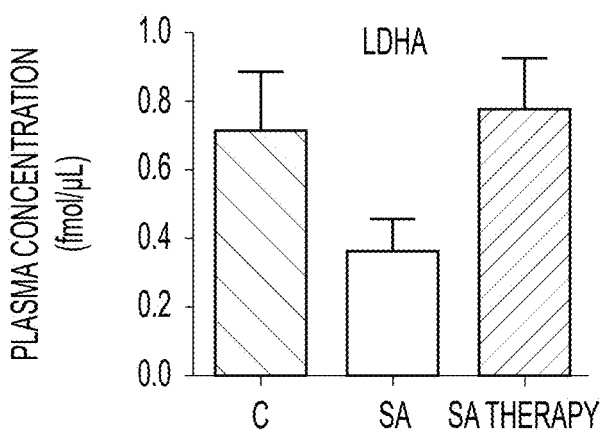
FIG. 3A is a graph showing levels of the LDHA protein in a Control group (C), individuals diagnosed with SA, and individuals having undergone SA therapy.
Figure 3B:
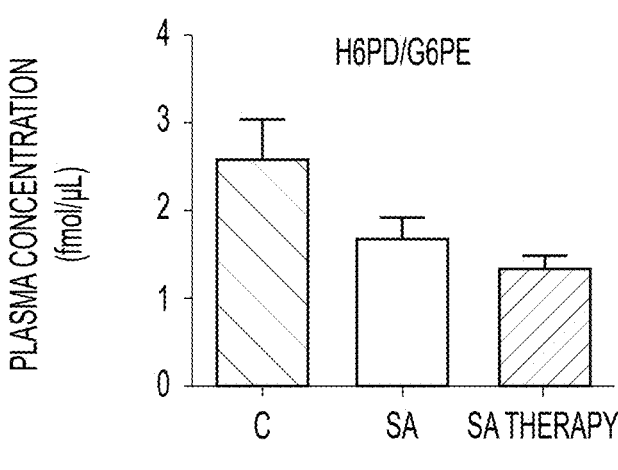
FIG. 3B is a graph showing levels of the H6PD/G6PE protein in a Control group (C), individuals diagnosed with SA, and individuals having undergone SA therapy.
Figure 3C:
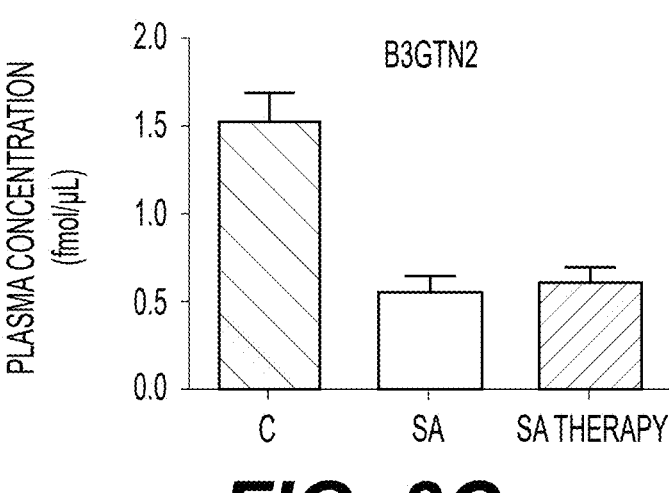
FIG. 3C is a graph showing levels of the B3GNT2 protein in a Control group (C), individuals diagnosed with SA, and individuals having undergone SA therapy.

Referring to FIGS. 3A-3C, the levels of the three target proteins, LDHA (FIG. 3A), H6PD/G6PE (FIG. 3B), and B3GNT2 (FIG. 3C) in the three test groups, Control (C), SA, and SA therapy are compared in the graphs The levels of these proteins were compared to various sleep indices, such as sleep oxygenation, AI, and AHI scores, obtained through polysomnography conducted in a sleep laboratory. Strong and significant correlations were observed between the markers and the AI and AHI readings, supporting their diagnostic and predictive potential for identifying SA.

It is to be understood that the method of diagnosing and treating SA described are not limited to the descriptions herein, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of diagnosing and treating Sleep Apnea (SA) in a patient, the method comprising:

determining whether the patient needs a Polysomnography by:

(a) obtaining a biological sample from the patient; and (b) determining if the sample comprises a previously determined level of an amino acid sequence comprising a sequence at least 95% identical to a protein selected from the group consisting of B3GNT2, LDHA, and H6PD/G6PE, wherein the previously determined level is a level of the amino acid sequence detected in a group of patients that tested positive for SA in a Polysomnography, wherein expression of the previously determined level of one of the proteins confirms that the patient needs a Polysomnography, and provides an initial diagnosis of SA in the patient;

conducting a Polysomnography on the patient to confirm the initial diagnosis of SA; and when the initial diagnosis of SA is confirmed, treating the patient with a treatment of SA selected from the group consisting of ENT multilevel surgery, continuous positive airway pressure therapy, and bariatric surgery.

---

SEQUENCE LISTING

```
Sequence total quantity: 3
SEQ ID NO: 1              moltype = AA   length = 397
FEATURE                   Location/Qualifiers
source                    1..397
                          mol_type = protein
                          organism = Homo sapiens
SEQUENCE: 1
MSVGRRRIKL LGILMMVNVF IYLIVEVSKS SSQEKNGKGE VIIPKEKFWK ISDPPVAYWN  60
REQEKLNRRY NPILNTLANQ TGDVYGFSNI SHLNFCEPDL RVMSVVSGFS NLPDRFKDFL  120
LYLRCRNYSL LIDQPDKCAK KPFLLLAIKS LIPHFARRQA IRESWGRETN VGNQTVVRVF  180
LLGQTPPEDN HPDLSDMLKF ESEKHQDILM WNYRDTFFNL SLKEVLFLRW VSTSCPNAEF  240
VFKGDDDVFV NTHHILNYLN SLPKNKAKDL FIGDVIHNAG PHRDKKLKYY IPEVVYTGVY  300
PPYAGGGGFL YSGHLALRLY NITDQVLLYP IDDVYTGMCL QKLGLVPEKH KGFKTFDIEE  360
KNKNNICSYV DLMLVHSRKP QEMIDIWSRL QNAHLNC                           397

SEQ ID NO: 2              moltype = AA   length = 332
FEATURE                   Location/Qualifiers
source                    1..332
                          mol_type = protein
                          organism = Homo sapiens
SEQUENCE: 2
MATLKDQLIY NLLKEEQTPQ NKITVVGVGA VGMACAISIL MKDLADELAL VDVIEDKLKG  60
EMMDLQHGSL FLRTPKIVSG KDYNVTANSK LVIITAGARQ QEGESRLNLV QRNVNIFKFI  120
IPNVVKYSPN CKLLIVSNPV DILTYVAWKI SGFPKNRVIG SGCNLDSARF RYLMGERLGV  180
HPLSCHGWVL GEHGDSSVPV WSGMNVAGVS LKTLHPDLGT DKDKEQWKEV HKQVVESAYE  240
VIKLKGYTSW AIGLSVADLA ESIMKNLRRV HPVSTMIKGL YGIKDDVFLS VPCILGQNGI  300
SDLVKVTLTS EEEARLKKSA DTLWGIQKEL QF                                332

SEQ ID NO: 3              moltype = AA   length = 515
FEATURE                   Location/Qualifiers
source                    1..515
                          mol_type = protein
                          organism = Homo sapiens
SEQUENCE: 3
MAEQVALSRT QVCGILREEL FQGDAFHQSD THIFIIMGAS GDLAKKKIYP TIWWLFRDGL  60
LPENTFIVGY ARSRLTVADI RKQSEPFFKA TPEEKLKLED FFARNSYVAG QYDDAASYQR  120
LNSHMNALHL GSQANRLFYL ALPPTVYEAV TKNIHESCMS QIGWNRIIVE KPFGRDLQSS  180
DRLSNHISSL FREDQIYRID HYLGKEMVQN LMVLRFANRI FGPIWNRDNI ACVILTFKEP  240
FGTEGRGGYF DEFGIIRDVM QNHLLQMLCL VAMEKPASTN SDDVRDEKVK VLKCISEVQA  300
NNVVLGQYVG NPDGEGEATK GYLDDPTVPR GSTTATFAAV VLYVENERWD GVPFILRCGK  360
ALNERKAEVR LQFHDVAGDI FHQQCKRNEL VIRVQPNEAV YTKMMTKKPG MFFNPEESEL  420
DLTYGNRYKN VKLPDAYERL ILDVFCGSQM HFVRSDELRE AWRIFTPLLH QIELEKPKPI  480
PYIYGSRGPT EADELMKRVG FQYEGTYKWV NPHKL                             515
```

2. The method of claim 1, wherein the biological sample is selected from the group consisting of plasma, blood, urine, and saliva.

3. The method of claim 2, wherein the biological sample is plasma.

4. The method of claim 1, further comprising taking an additional biological sample from the patient in a timeframe comprising 3 months to 6 months after the treatment of SA and detecting a level of the protein.

5. The method of claim 4, further comprising administering a treatment for SA to the patient.

6. A method of diagnosing and treating obstructive Sleep Apnea (SA) in a patient, the method comprising:

obtaining a biological sample from the subject;

detecting in the biological sample the presence of a previously determined level of an amino acid sequence comprising a sequence at least 95% identical to a protein selected from the group consisting of B3GNT2, LDHA, and H6PD/G6PE, wherein the previously determined level is a level of the amino acid sequence detected in a group of patients that tested positive for SA in a Polysomnography, wherein the previously determined level of one of the proteins confirms a diagnosis of SA in the patient; and treating the patient with a treatment of SA selected from the group consisting of ENT multilevel surgery, continuous positive airway pressure (CPAP) therapy, and bariatric surgery.

7. The method of claim 6, wherein the biological sample is selected from the group consisting of plasma, blood, urine, and saliva.

8. The method of claim 7, wherein the biological sample is plasma.

9. The method of claim 6, further comprising taking an additional biological sample from the subject in a timeframe comprising 3 months to 6 months after the treatment of SA and detecting a level of the protein.

10. The method of claim 9, further comprising administering a treatment to the patient.

11. The method of claim 6, wherein the biological sample is tested using mass spectrometry (MS) for proteomics.

12. The method of claim 6, wherein the treatment of SA used is based on the protein detected.

* * * * *